United States Patent [19]

Venier et al.

[11] Patent Number: 5,012,023
[45] Date of Patent: Apr. 30, 1991

[54] LUBRICANTS COMPRISING NOVEL CYCLOPENTANES, CYCLOPENTADIENES, CYCLOPENTENES, AND MIXTURES THEREOF AND METHODS OF MANUFACTURE

[75] Inventors: Clifford G. Venier; Edward W. Casserly, both of The Woodlands, Tex.

[73] Assignee: Pennzoil Products Company, Houston, Tex.

[21] Appl. No.: 323,906

[22] Filed: Mar. 15, 1989

Related U.S. Application Data

[63] Continuation-in-part of Ser. No. 909,305, Sep. 19, 1986, Pat. No. 4,721,823, and a continuation-in-part of Ser. No. 170,652, Mar. 15, 1988, abandoned.

[51] Int. Cl.$^5$ .................... C07C 13/11; C07C 13/08
[52] U.S. Cl. .......................... 585/20; 585/7; 585/23; 585/359; 585/375
[58] Field of Search ................ 585/20, 7, 23, 359, 585/375

[56] References Cited

U.S. PATENT DOCUMENTS

| | | | |
|---|---|---|---|
| 2,088,598 | 8/1937 | Ipatieff et al. | 585/375 |
| 2,953,607 | 9/1960 | Hafner | 585/359 |
| 3,000,981 | 9/1961 | Favis | 585/23 |
| 3,004,384 | 10/1961 | Saunders | 585/255 |
| 3,131,227 | 4/1964 | Vries | 585/23 |
| 3,214,483 | 10/1965 | Cripps | 585/23 |
| 3,251,897 | 5/1966 | Wise | 585/375 |
| 3,255,267 | 6/1966 | Fritz | 585/23 |
| 3,356,704 | 12/1967 | Marcus | 585/357 |
| 3,358,008 | 12/1967 | Marcus | 585/357 |
| 3,388,180 | 6/1968 | Marcus | 585/20 |
| 3,391,209 | 7/1968 | Marcus | 585/20 |
| 3,403,105 | 9/1968 | Sandri | 252/75 |
| 3,414,626 | 12/1968 | Marcus | 585/357 |
| 3,419,622 | 12/1968 | Marcus | 585/20 |
| 3,560,583 | 2/1971 | Stewart | 585/359 |
| 3,636,176 | 1/1972 | Hall | 585/22 |
| 3,751,500 | 8/1973 | Hall | 585/22 |
| 3,755,492 | 8/1973 | Anderson | 585/703 |
| 3,931,334 | 1/1976 | Gemmill, Jr. | 568/57 |
| 4,063,010 | 12/1977 | Marie et al. | 526/169 |
| 4,147,640 | 4/1979 | Jayne et al. | 252/45 |
| 4,246,373 | 1/1981 | Kennedy et al. | 585/359 |
| 4,412,088 | 10/1983 | Gruber et al. | 585/23 |
| 4,547,603 | 10/1985 | Rajan | 585/375 |
| 4,567,308 | 1/1986 | Yoshida et al. | 585/375 |
| 4,604,492 | 8/1986 | Shimizu et al. | 585/360 |
| 4,721,823 | 1/1988 | Venier et al. | 585/20 |

FOREIGN PATENT DOCUMENTS 55535 9/1968 Poland .
55571 9/1968 Poland .

OTHER PUBLICATIONS

Denis, Journal of Synthetic Lubrication, vol. 1, pp. 201-219, 1985.
Hirsch, Thesis, University of Maryland (1963).

*Primary Examiner*—Asok Pal
*Attorney, Agent, or Firm*—Lowe, Price, Leblanc, Becker & Shur

[57] ABSTRACT

Hydrocarbyl substituted cyclopentadienes, cyclopentenes, and cyclopentanes are synthetic lubricating compositions. The preferred structures contain 1 to 6 alkyl groups which have 4 to 36 carbon atoms and may have different and varying carbon chain structures. The cyclopentenes and cyclopentanes are prepared by hydrogenation from the corresponding cyclopentadiene intermediates. The cyclopentadienes are prepared by reaction with hydrocarylating agents or alcohols. Mixtures are also disclosed.

17 Claims, 1 Drawing Sheet

5,012,023

LUBRICANTS COMPRISING NOVEL CYCLOPENTANES, CYCLOPENTADIENES, CYCLOPENTENES, AND MIXTURES THEREOF AND METHODS OF MANUFACTURE

CROSS REFERENCE TO RELATED APPLICATION

This is a continuation-in-part of U.S. application Ser. No. 909,305, filed Sept. 19, 1986, now U.S. Pat. No. 4,721,823, and a continuation-in-part of Ser. No. 170,652 filed Mar. 15, 1988, now abandoned.

FIELD OF THE INVENTION

This invention relates to novel hydrocarbyl-substituted cyclopentadienes, hydrocarbyl-substituted cyclopentadienes, hydrocarbyl-substituted cyclopentenes, and mixtures thereof, and their use as lubricating compositions, and more particularly, this invention relates to novel hydrocarbyl cyclopentanes, hydrocarbyl cyclopentadienes, hydrocarbyl cyclopentenes, and mixtures thereof, novel methods for formation of the cyclopentadienes and their conversion to the cyclopentenes and cyclopentanes, and use of the cyclopentanes, cyclopentadienes, cyclopentenes and mixtures thereof as lubricating compositions.

BACKGROUND

Cyclopentadiene, cyclopentene and cyclopentane and alkylated derivatives thereof are known in the art. Further, methods are known for preparation of alkylated cyclopentadienes and conversion of these materials to cyclopentenes and cyclopentanes. There is substantial interest in cyclopentadienes, cyclopentenes, and cyclopentanes since cyclopentadiene is characterized by the unique property of being the most acidic aliphatic hydrocarbon known, having a pKa of 18, and also because its reactions as a Diels-Alder diene are extremely facile. Because of the aromaticity of the cyclopentadiene anion (c—$C_5H_5^-$), cyclopentadiene is easily the most acidic of the simple hydrocarbons and in fact is comparable in acidity to alcohols. This means that substantial amounts of the anion can be generated with alkoxides and even concentrated solutions of hydroxide. Since it is uniquely stable, it can participate in the carbanion reactions of alkylation, acylation, carboxylation and the like.

U.S. Pat. No. 3,255,267 to Fritz et al discloses the alkylation of cyclopentadiene and monoalkylcyclopentadiene with a single primary or secondary alcohol in the presence of a highly alkaline catalyst, including the disclosure of trialkylated and tetralkylated products. Fritz et al do not appear to contemplate using mixed alcohols for alkylation and the alkylcyclopentadiene products disclosed cannot have more than two different alkyl groups, a single substituent derived from starting cyclopentadiene and the rest derived from the alcohol.

The cyclopentadienes described by Fritz et al contain primary hydrocarbon substituents of up to 11 carbon atoms and secondary hydrocarbons of structure $R_cR_dCH$, where $R_c$ is selected from "hydrocarbon radicals free of aliphatic unsaturation, including alkyl and aryl radicals, said radicals having from 1 to 10 carbon atoms;" and $R_d$ is "a hydrocarbon radical free of aliphatic unsaturation, including alkyl and aryl radicals, said radicals having from 1 to 10 carbon atoms,". An additional class includes $R_cR_d = -CH_2(CH_2)_nCH_2-$ where n is an integer having a value of 1 to 10. Thus, Fritz et al teach compositions in which no more than two different kinds of hydrocarbyl groups may be present, and in which no more than one hydrocarbyl group may occur more than once. Thus, the products which can be produced by Fritz et al are controlled by this disclosed alkylation reaction which uses only a single alcohol. In addition, Fritz et al teach that "Ethanol is by far the preferred primary alcohol since the yields obtained with this alcohol are much in excess of the yields obtained when employing other primary alcohols." Fritz et al present two examples of alkylation with primary alcohols with the following yields based on cyclopentadiene:

Example 24: Ethanol plus cyclopentadiene—17.8% yield

Example 26: 2-Ethylbutanol plus cyclopentadiene—1.6% yield.

Applicants have discovered that the process improvement of removing water from the reaction as it is formed greatly increases the yields obtained with primary alcohols to near quantitative levels and that using mixtures of alcohols provides an alkylation reaction which produces a wide variety of novel and useful alkylated cyclopentadienes.

U.S. Pat. No. 3,560,583 discloses cyclopentadiene compounds containing up to five substituents, which substituents can be independently hydrogen, alkyl, aryl or aralkyl. These compounds are prepared by reaction of a cyclopentadiene compound with benzyl halide or allyl halide, an alkali metal hydroxide and a quaternary ammonium salt catalyst.

Polish patent No. 55,535 to Makosza, 1968, discloses indene compounds which contain alkyl substituents on the cyclopentadiene portion of the molecule. However, the working examples indicate that only a single alkyl group or two allyl groups are present. U.S. Pat. No. 3,931,334 discloses lubricant compositions which comprise substituted indans, the indan molecule being substituted by methyl and styryl.

In a thesis by Stephen S. Hirsch, University of Maryland, 1963, there is disclosure of base catalyzed alkylation of cyclopentadienes utilizing alcohols to effect the alkylation. Included in this disclosure are alkylation reactions with benzyl alcohol to produce cyclopentadienes which can contain as many as five benzyl substituents. Also disclosed are 1,3-dialkyl indenes.

Polish patent No. 55,571 to Makosza discloses cyclopentadienes and processes for preparation of monosubstituted cyclopentadienes by the use of phase-transfer alkylation. The patent is limited to monosubstituted compounds with short chain alkyl groups.

The prior art contains numerous disclosures of methods for the preparation of substituted cyclopentadienes but wherein the substituents usually are short chain alkyl groups. The methods of preparation of such materials vary but do include such processes as the reaction of the cyclopentadiene with alkyl halides in the presence of a base as in U.S. Pat. No. 2,953,607. Similar disclosures may be found in U.S. Pat. Nos. 3,131,227, 4,547,603, 4,567,308, 3,560,583, 4,412,088, and 3,755,492. Of particular interest is 3,131,227 which discloses polysubstituted cyclopentadienes such as pentamethyl and hexamethyl cyclopentadiene which is prepared by a cyclization reaction. Also in U.S. Pat. No. 4,567,308, alkyl cyclopentadienes and alkylated derivatives thereof are prepared by the vapor phase reaction of a cyclopentadiene derivative and an aliphatic lower alcohol in the presence of a basic catalyst. These cyclopentadienes and alkylated products are disclosed as being additives for synthetic rubbers, starting materials for resins and/or industrial chemicals.

In a publication by J. Denis, Journal of Synthetic Lubrication, Vol. 1, p. 201-219 (1985), there is disclosure of hydrocarbons which may be used in lubricant compositions. Specifically mentioned in this publication are cycloalkanes and in particular monoalkyl substituted cyclopentanes. This publication in a comparison of various hydrocarbon structures including normal alkanes, alkanes branched by one or more alkyl chains or by a ring, cycloalkanes and aromatics as base stocks for lubricants.

In a publication by Rong et al, Acta Chemica Sinica, Vol. 41, No. 10, Oct., 1983, there is disclosure of the use of polyethylene glycol as a phase transfer agent for halide alkylation of cyclopentadiene with alkyl halides. The products produced are monoalkyl substituted cyclopentadienes. In a related article by Rong et al, Journal of Chinese Universities, Vol. 4, page 576-580 (1983), there is disclosure of the synthesis of alkyl substituted derivatives of cyclopentadiene by the phase transfer catalytic reaction of cyclopentadiene with alkyl halides in the presence of potassium hydroxide and polyoxyethylene surfactants as a catalyst. Only monoalkyl substituted cyclopentadienes are prepared.

U.S. Pat. Nos. 3,004,384, 3,356,704, 3,358,008, 3,388,180, 3,391,209, 3,414,626, and 3,419,622 disclose polysubstituted cyclopentadienes and cyclopentanes but wherein the substituent is a short chain alkyl group or allyl group. Finally, U.S. Pat. Nos. 3,751,500 and 3,636,176 disclose indene compounds which can contain short chain alkyl substituents which are useful as perfume compositions.

In none of the prior art of which Applicants are aware are there disclosures of poly-hydrocarbyl cyclopentanes, cyclopentadienes, cyclopentenes, and mixtures thereof which are useful as lubricant compositions, which useful products may be prepared from novel hydrocarbyl-substituted cyclopentadienes. The present invention provides such novel products as well as methods for their preparation and methods for their use.

SUMMARY OF THE INVENTION

It is accordingly one object of the present invention to provide hydrocarbon-substituted cyclopentanes which are useful as lubricating compositions.

A further object of the invention is to provide novel and useful cyclopentanes which are poly-hydrocarbyl substituted and which are prepared from the corresponding hydrocarbyl substituted cyclopentadienes.

A still further object of the present invention is to provide lubricating compositions which contain hydrocarbyl-cyclopentanes as a lubricating component.

There are also provided novel intermediate compositions of matter which comprise hydrocarbyl-substituted cyclopentadienes and hydrocarbyl-substituted cyclopentenes, the cyclopentadienes and cyclopentenes also being useful as lubricating compositions.

Also provided by the present invention are lubricating compositions which comprise novel poly-hydrocarbyl substituted cyclopentadienes and poly-hydrocarbyl substituted cyclopentenes.

Also provided by the present invention are lubricating compositions comprising mixtures of hydrocarbyl cyclopentanes, hydrocarbyl cyclopentenes, and/or hydrocarbyl substituted cyclopentadienes, optionally in admixture with a natural lubricant such as mineral oil or other synthetic lubricants as base fluids.

Further provided by the present invention are novel methods for preparation of the hydrocarbon-substituted cyclopentadienes comprising a phase transfer method and an alcohol method.

Other objects and advantages of the present invention will become apparent as the description thereof proceeds.

In satisfaction of the foregoing objects and advantages of the present invention, there is provided as a broad embodiment of the invention, a class of lubricating compositions which comprise one or more hydrocarbyl-substituted cyclopentanes. These hydrocarbyl-substituted cyclopentanes include the individual compounds and mixtures of the hydrocarbyl-substituted cyclopentane compounds. The compounds are of the following general formula:

wherein in the above formula, each $R_1$ is individually and independently selected from alkyl groups of 1 to 4 carbons, each $R_2$ is individually and independently selected from hydrocarbyl groups containing about 4 to 36 carbon atoms, preferably 8 to 36 carbon atoms, more preferably 12 to 24 carbon atoms, z is 0, 1, 2 or 3, and x is an integer ranging from 1 to 6, preferably 2 to 6, more preferably 3 to 6, and x+z cannot be greater than 6. Preferred compounds within this group are those wherein each $R_2$ is individually and independently selected from alkyl groups having about 8 to 24 carbon atoms, x is an integer of about 2 to 6, and more preferably is an integer ranging from 3 to 6, and the total number of carbon atoms in the $R_2$ groups should preferably not exceed about 80.

In a further embodiment of the invention, there are provided novel cyclopentane compositions which are useful as lubricating compositions and which are of the following general formula:

wherein each $R_1$ is individually and independently selected from alkyl groups of 1 to 4 carbons, each $R_2$ is individually and independently selected from hydrocarbyl groups having about 4 to 36 carbon atoms, preferably straight or branch chained alkyl groups, z is 0, 1, 2 or 3 and y is an integer ranging from 2 to 6, preferably 3 to 6, provided that when at least 2 of the $R_2$ substituents contain alkyl groups of from 4 to 10 carbon atoms, then y must be an integer of at least 3, y+z cannot be greater than 6. The total number of carbon atoms in the $R_2$ groups should preferably not exceed about 80.

There are further provided by the present invention novel cyclopentadiene intermediate compounds which can be hydrogenated to the cyclopentanes referred to above, which intermediate cyclopentadienes are of the following general formula:

wherein in the above formula, each $R_1$ is individually and independently selected from alkyl groups of 1 to 4 carbon atoms, each $R_2$ is individually and independently selected from hydrocarbyl groups, preferably straight or branch chained alkyl or alkenyl groups of 4 to 36 carbon atoms, preferably 8 to 36 carbon atoms, more preferably 12 to 24 carbon atoms, z is 0, 1, 2 or 3, and y is an integer of from 2 to 6, preferably 3 or 4 to 6, and y+z cannot be greater than 6, provided that when up to four of the $R_2$ groups contain from 4 to 11 carbon atoms, then y must be an integer of at least 5. The total number of carbon atoms in the $R_2$ groups should preferably not exceed about 80.

The cyclopentadiene compounds of the above formula, referred to as novel intermediate compounds, are also included in a group of novel lubricating compositions. Thus, polyhydrocarbyl substituted cyclopentadienes of the following formula are useful as lubricating compositions:

wherein in the above formula, each $R_1$ is individually and independently selected from alkyl groups of 1 to 4 carbon atoms, each $R_2$ is individually and independently selected from hydrocarbyl groups containing about 4 to 36 carbon atoms, preferably 8 to 36 carbon atoms, more preferably 12 to 24 carbon atoms, z is 0, 1, 2 or 3, and x is an integer ranging from about 1 to 6, preferably 2 to 6, more preferably 3 or 4 to 6, and x+z cannot be greater than 6. Preferred compounds within this group are those wherein each $R_2$ is individually and independently selected from alkyl or alkenyl groups having about 8 to 24 carbon atoms and x is an integer of about 2 to 5, and the total number of carbon atoms in the $R_2$ groups should preferably not exceed about 80. The cyclopentadienes of this formula may also be used as intermediates for hydrogenation to the cyclopentene and cyclopentane lubricants of the invention.

There are also provided by the present invention lubricating compositions which are partially synthetic lubricants and partially natural lubricants. These lubricating compositions comprise the hydrocarbyl substituted cyclopentanes, or the hydrocarbyl substituted cyclopentandienes, or the hydrocarbyl substituted cyclopentenes, or any mixture thereof, in any proportions with a natural lubricant base such as mineral oil. Also provided are mixtures of the synthetic lubricating compositions of the present invention with other synthetic lubricants so that the resulting lubricating composition is a mixture of synthetic lubricants. Also included within the scope of the invention are mixtures of any or all of the synthetic lubricants of the present invention, alone or in admixture with other synthetic lubricants, or with natural lubricants.

Also provided by the present invention are methods for production of the hydrocarbyl-substituted cyclopentadiene compounds, one method comprising the single step reaction of cyclopentadiene or substituted cyclopentadiene with a molar excess of a hydrocarbylating agent or mixture of such agents of the formula $R_2Y$, wherein $R_2$ is as described above and Y is a leaving group, preferably a halogen, in a reaction vessel containing an aqueous alkaline solution and a phase transfer catalytic agent. In a second method for preparation of the novel cyclopentadienes, cyclopentadiene or substituted cyclopentadiene is reacted with a molar excess of a primary or secondary alcohol or mixture of such alcohols of the formula $R_2OH$ wherein $R_2$ is as described above in the presence of a basic catalyst at elevated temperatures, and with removal of water as it is formed, and recovering the product.

BRIEF DESCRIPTION OF THE DRAWINGS

Reference is now made to the drawings accompanying the application wherein.

DESCRIPTION OF PREFERRED EMBODIMENTS

Figure 1:
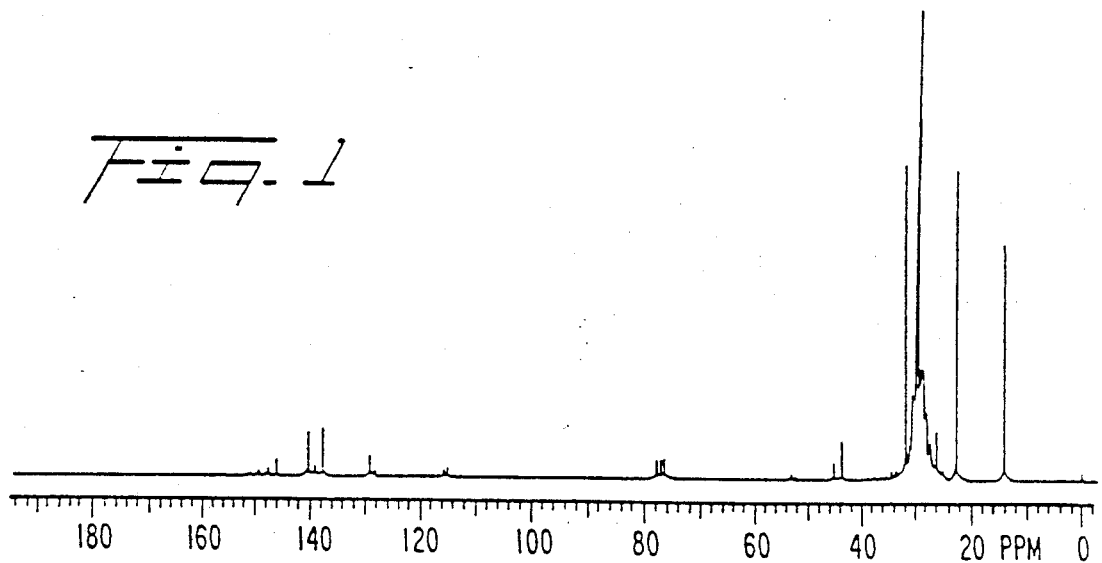
FIG. 1 is the $^{13}C$ nmr spectrum of alkylcyclopentadiene.

The present invention is broadly concerned with lubricating compositions which comprise certain hydrocarbyl cyclopentanes, hydrocarbyl cyclopentadienes, hydrocarbyl cyclopentenes, or mixtures thereof, and methods of preparation. The invention is also concerned with a class of novel cyclopentanes and corresponding cyclopentadiene and cyclopentene intermediates, methods for their preparation and methods for conversion of the cyclopentadienes to the cyclopentane lubricants.

In a main embodiment of the invention, novel synthetic fluids which are lubricating compositions comprise a group of polyhydrocarbyl-substituted cyclopentanes of the following formula:

I wherein in the above formula, each $R_1$ is individually and independently selected from alkyl groups of 1 to 4 carbon atoms, each $R_2$ is individually and independently selected from hydrocarbyl groups containing from about 4 to about 36 carbon atoms, preferably 8 to 36 carbon atoms, more preferably 12 to 24 carbon atoms; and preferably is a straight or branch chained alkyl group of 4 to 36 carbon atoms, preferably 8 to 36 carbon atoms; z is 0, 1, 2 or 3, and x is an integer ranging from 2 to 6, preferably 3 to 6, and x+z cannot be greater than 6.

It will be understood that in Formula I as well as in Formulae II to VIII described hereinafter, the $R_2$ hydrocarbon groups can be straight or branch-chained, can be of the same or different chain length, and can contain alicyclic rings of 3 to 7 carbon atoms, such as cycloalkyl. Since the cyclopentanes are produced by hydrogenation, little if any unsaturation, except possibly for aromatic double bonds, will remain in the hydrocarbon substituents. In the definition of $R_1$ in the Formula I compounds, as well as the compounds of Formulae II to VIII described hereinafter, it will be understood that the alkyl groups may be the same or different and straight or branch-chained.

These hydrocarbon substituted cyclopentanes have been found to provide excellent lubricating characteristics which make them useful as lubricants in internal combustion engines and in other areas where good lubricity is a requirement. The lubricants may comprise individual hydrocarbyl-substituted cyclopentanes or mixtures thereof. The compounds provide the appropriate specific gravity, refractive indices, viscosities, and low and high temperature characteristics which are required for an outstanding lubricant. In particular the lubricants exhibit specific gravities ranging from about 0.835 to about 0.860; refractive indices ranging from about $n_D^{25}C$ 1.450 to 1.40; viscosities at 100° C. (cSt) ranging from 2.0 to 20.0, at 40° C. (cST) ranging from 6.0 to 350, at 0° C. (cP) ranging from 200 to 13,000, and at −40° C. (cP), ranging from 1500 to 600,000. The viscosity index ranges from 45 to 200. The compositions also provide excellent low temperature pour points. Flash points range from 400° to 600° F. and fire points range from 450° to 650° F. with minimum loss to evaporation at these temperatures.

In the hydrocarbon substituted cyclopentane compositions described above, some compounds of the above formula which contain a single methyl group substituent provide lubricants which have a lowered pour point as compared to otherwise comparable cyclopentanes. This causes the cyclopentanes to be particularly useful in certain lubricating environments.

A preferred group of hydrocarbon substituted cyclopentane lubricants are those wherein x is an integer of 3 to 5, $R_1$ is methyl and z is 0 or 1, and $R_2$ is an alkyl group of 8 to 24 carbon atoms, and wherein x is an integer of 2 to 4, $R_1$ is methyl and z is 0 or 1, and $R_2$ is an alkyl group of 13 to 24 carbon atoms.

In further embodiments of the invention, the intermediate hydrocarbon-substituted cyclopentadienes and hydrocarbon substituted cyclopentenes are also provided as lubricating compositions. These compounds have lubricating characteristics including viscosities and pour points which make them useful in a variety of areas.

The lubricating compositions which comprise cyclopentadienes are of the following formula:

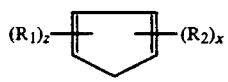
II wherein z, $R_1$ and $R_2$ are as defined above in Formula I and x is an integer ranging from 1 to 6.

Also provided by the present invention are cyclopentene compositions which are useful as synthetic lubricants. These cyclopentenes may be described by the following general formula:

III wherein $R_1$, $R_2$, z and x are as defined above.

There is also provided by the present invention partial synthetic lubricant compositions in which the hydrocarbon-substituted cyclopentanes, the hydrocarbon-substituted cyclopentenes, or the hydrocarbon-substituted cyclopentadienes, used either alone or in admixture, are mixed with a natural base fluid such as mineral oil to form the lubricant. Compositions of this type may contain about 10 to 90% of any of the synthetic lubricants of this invention mixed with 90 to 10% of a mineral oil base fluid. Compositions of this type show enhanced lubricant properties.

In a further embodiment of the invention, mixtures of the hydrocarbon-substituted cyclopentanes, the hydrocarbon-substituted cyclopentenes, or the hydrocarbon-substituted cyclopentadienes, used either alone or in admixture, may be mixed with other synthetic lubricants such as poly-alpha-olefin, esters and polyol esters. These mixtures may include 10 to 90% of the synthetic hydrocarbon substituted cyclopentanes, cyclopentenes, and/or cyclopentadienes of this invention, mixed with 90 to 10% of any other compatible synthetic lubricant.

In a still further embodiment of the invention, lubricating compositions are provided which comprise mixtures of the hydrocarbon-substituted cyclopentanes, hydrocarbon-substituted cyclopentenes, and hydrocarbon-substituted cyclopentadienes of this invention, the mixtures being in varying and all proportions. Mixtures of this type arise from incomplete hydrogenation in production of the cyclopentanes from the cyclopentadienes as described hereinafter. This hydrogenated mixture will comprise mixtures of these compounds which can be used as such as a lubricating composition.

Preferred lubricating compositions according to the invention are those cyclopentanes, cyclopentenes and cyclopentadienes which contain a plurality of $R_2$ hydrocarbyl groups, i.e., wherein x is 3 to 6. Even more preferred are those compounds wherein the $R_2$ substituents are hydrocarbyl groups of different carbon chain length.

In a further embodiment of the invention, there are also provided a group of novel hydrocarbyl substituted cyclopentanes which are of the following formula:

IV wherein in the above formula, $R_1$ is individually and independently selected from alkyl groups of 1 to 4 carbon atoms, $R_2$ is individually and independently selected from hydrocarbyl groups of 4 to 36 carbon atoms, preferably 8 to 36 carbon atoms, and more preferably 12 to 24 carbon atoms, and preferably are straight or branch chained alkyl groups containing 4 to 36 carbon atoms, preferably 8 to 24 carbon atoms, which can contain alicyclic rings of 3 to 7 carbon atoms, such as cycloalkyl, z is 0, 1, 2 or 3, and y is an integer of from 2 to 6, provided that when at least two of the $R_2$ groups are carbon chains of from about 4 to 10 carbon atoms, then the integer y must be at least 3, and y+z cannot be greater than 6.

The hydrocarbon-substituted cyclopentanes of the present invention are prepared by hydrogenation of the corresponding hydrocarbon-substituted cyclopentadienes by conventional hydrogenation techniques. The hydrogenation reactions of this type are known in the art and generally comprise reaction of the hydrocarbon-substituted cyclopentadiene intermediate or mixture of intermediates in the presence of a hydrogenation catalyst such as Raney nickel or palladium and in the presence or absence of an organic solvent such as an aliphatic hydrocarbon. In carrying out the hydrogenation reaction, the reactor is pressurized with hydrogen to a pressure which may range up to about 3000 psi and heated in the range of 75° to 200° C. until the hydrogenation is complete as evidenced by cessation of hydrogen uptake. On removal of the catalyst and solvent, the hydrogenated cyclopentane is recovered.

The hydrocarbon-substituted cyclopentadienes which serve as precursors, many of which are also novel compounds, may be characterized by the following general formula:

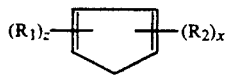

V

In the above formula, $R_1$ is individually and independently selected from alkyl groups of 1 to 4 carbon atoms, $R_2$ is individually and independently selected from hydrocarbon substituents of 4 to 36 carbon atoms, preferably 8 to 36 carbon atoms, and more preferably 12 to 24 carbon atoms, preferably straight or branch-chained alkyl groups, alkenyl groups, or alkynyl groups having from 4 to 36 carbon atoms, preferably 8 to 24 carbon atoms, which can contain alicyclic rings of 3 to 7 carbons such as cycloalkyl and/or aromatic rings of 6 to 12 carbon atoms, z is 0, 1, 2, or 3, $x+z$ cannot be greater than 6, and x is an integer ranging from 1 to 6. It is preferred that at least two of the $R_2$ groups contain from 8 to 13 carbon atoms, and that x be an integer of 3 to 5.

A novel group of cyclopentadiene compounds are those of the formula:

VI wherein each $R_1$ is individually and independently selected from alkyl groups of 1 to 4 carbon atoms, each $R_2$ is individually and independently selected from hydrocarbyl groups of 8 to 36 carbon atoms, preferably 12 to 24 carbon atoms, attached to the ring through a primary carbon, z is 0, 1, 2, or 3, and y is an integer of from 2 to 6, $y+z$ cannot be greater than 6, and provided that when up to four of the $R_2$ groups contain 4 to 11 carbon atoms, then y must be an integer of at least 5. An important aspect of the alkylated cyclopentadiene compounds is that the $R_2$ substituents are attached to the cyclopentane ring through a primary carbon.

An especially select group of novel cyclopentadienes are those of the structure

such that each of the $R_a$ groups are individually and independently selected from hydrocarbyl groups of 1 to 4 carbon atoms and $n=0$ to 4, each of the $R_b$ groups are individually and independently selected from hydrocarbyl groups of 7 to 35 carbon atoms, preferably 8 to 24 carbon atoms, and $m=0$ to 6, and each of the $(CHR_cR_d)$ groups are individually and independently selected from hydrocarbyl groups of 8 to 36 carbon atoms, preferably 8 to 24 carbon atoms, in which $R_c$ and $R_d$ are individually and independently selected from hydrocarbyl groups of 1 to 24 carbon atoms, preferably 8 to 24 carbon atoms, and $p=0$ to 5, provided that $n+m+p$ is 2 to 6 and $m+p$ is 2 to 6, and provided that if $n=0$ and $p=0$ and there are no more than two different $R_b$ groups and no more than one $R_b$ occurs more than once, and all the $R_b$ have 10 or fewer carbon atoms, then m must be 5 or 6, and provided that if $n=0$ and $p=1$ and both the $R_c$ group and the $R_d$ group have 10 or fewer carbon atoms and all the $R_b$ groups are the same and have 10 or fewer carbon atoms, then m must be 4 or 5, and provided that if $n=1$ and $p=0$ and all the $R_b$ groups are the same and have 10 or fewer carbon atoms, then m must be 4 or 5, and provided that if $n=0$ and $m=0$ and there are no more than two different $(CHR_cR_d)$ groups and no more than one $(CHR_cR_d)$ occurs more than once and all the $R_c$ groups and $R_d$ groups have 10 or fewer carbon atoms, then p must be 4 or 5, and provided that if $n=0$ and $m=1$ and the $R_b$ group has 10 or fewer carbons, and all the $R_c$ groups are the same and have 10 or fewer carbon atoms and all the $R_d$ groups are the same and have 10 or fewer carbon atoms, then p must be 3 or 4, and provided that if $n=1$ and $m=0$ and all the $(CHR_cR_d)$ groups are the same and the $R_c$ and $R_d$ groups both have 10 or fewer carbon atoms, then p must be 3 or 4.

The intermediate hydrocarbon-substituted cyclopentenes, most of which are also novel compounds, may be characterized by the following general formula:

VII

In the above formula, $R_1$ is individually and independently selected from alkyl groups of 1 to 4 carbon atoms, $R_2$ is individually and independently selected from hydrocarbon substituents of 4 to 36 carbon atoms, preferably 8 to 36 carbon atoms, more preferably 12 to 24 carbon atoms, preferably straight or branch-chained alkyl groups having from 4 to 36 carbon atoms, preferably 8 to 24 carbon atoms, which can contain alicyclic rings of 3 to 7 carbons such as cycloalkyl, and/or aromatic rings of 6 to 12 carbons, z is 0, 1, 2 or 3, and x is an integer ranging from 1 to 6, and $x+z$ cannot be greater than 6. It is preferred that at least two of the $R_2$ groups contain from 4 to 10 carbon atoms, and that x be an integer of 3 to 5. A preferred group of compounds includes those wherein the $R_2$ groups contain from 8 to 12 carbon atoms and x is 3 to 5.

A novel group of cyclopentene compounds are those of the formula:

VIII wherein z, $R_1$ and $R_2$ are as defined above, and y is an integer of 2 to 6, provided that when at least two of the $R_2$ groups contain from 4 to 10 carbon atoms then y is an integer of at least 3. In a particularly preferred group, when $R_2$ is an alkyl group which contains from 4 to 10 carbon atoms, then the integer x is 3, 4 or 5, the latter particularly representing a group of novel cyclopentene intermediates.

In the cyclopentanes, cyclopentenes and cyclopentadienes of the invention, the total number of carbon atoms in the $R_2$ substituents should preferably not exceed about 80.

Preferred compounds or mixtures of compounds according to the invention include cyclopentane, cyclopentadiene, and cyclopentene lubricants which, with reference to Formulae I, II, and III, may be defined as follows:

(1)
 $z=0$;
 $x=3$ or 4;
 $R_2=C_8$ and/or $C_{10}$ alkyl hydrocarbon.

(2)
 $z=0$;
 $x=3$ or 4;
 $R_2=C_9$ and/or $C_{10}$ and/or $C_{11}$ alkyl hydrocarbon.

(3)
 $z=0$;
 $x=3$ or 4;
 $R_2=C_{12}$ and/or $C_{13}$ alkyl hydrocarbon.

(4)
 $z=0$;
 $x=2$ or 3;
 $R_2=$ 2-octyl-1-dodecyl.

Particularly preferred specific classes of compounds and specific compounds or mixtures which are also useful as lubricants include the following:

Cyclopentanes

Tri-n-octyl cyclopentane
Tetra-n-octyl cyclopentane
Penta-n-octyl cyclopentane
Tri-n-nonyl cyclopentane
Tetra-n-nonyl cyclopentane
Penta-n-nonyl cyclopentane
Tri-n-decyl cyclopentane
Tetra-n-decyl cyclopentane
Penta-n-decyl cyclopentane
Tri-n-undecyl cyclopentane
Tetra-n-undecyl cyclopentane
Penta-n-undecyl cyclopentane
Tri-n-dodecyl cyclopentane
Tetra-n-dodecyl cyclopentane
Penta-n-dodecyl cyclopentane
Tri-2-ethylhexyl cyclopentane
Tetra-2-ethylhexyl cyclopentane
Di-n-octyl, n-decyl cyclopentane
n-octyl, di-n-decyl cyclopentane
Trioctyl, n-decyl cyclopentane
Di-n-octyl, di-n-decyl cyclopentane
n-octyl, tri-n-decyl cyclopentane
Tri-n-tridecyl cyclopentane
Tetra-n-tridecyl cyclopentane
Penta-n-tridecyl cyclopentane
Di-(2-octyl-1-dodecyl)cyclopentane
Tri-(2-octyl-1-dodecyl)cyclopentane
Tetra-(2-octyl-1-dodecyl)cyclopentane

Cyclopentenes

Tri-n-octyl cyclopentene
Tetra-n-octyl cyclopentene
Penta-n-octyl cyclopentene
Tri-n-nonyl cyclopentene
Tetra-n-nonyl cyclopentene
Penta-n-nonyl cyclopentene
Tri-n-decyl cyclopentene
Tetra-n-decyl cyclopentene
Penta-n-decyl cyclopentene
Tri-n-undecyl cyclopentene
Tetra-n-undecyl cyclopentene
Penta-n-undecyl cyclopentene
Tri-n-dodecyl cyclopentene
Tetra-n-dodecyl cyclopentene
Penta-n-dodecyl cyclopentene
Tri-2-ethylhexyl cyclopentene
Tetra-2-ethylhexyl cyclopentene
Di-n-octyl, n-decyl cyclopentene
n-octyl, di-n-decyl cyclopentene
Trioctyl, n-decyl cyclopentene
Di-n-octyl, di-n-decyl cyclopentene
n-octyl, tri-n-decyl cyclopentene
Tri-n-tridecyl cyclopentene
Tetra-n-tridecyl cyclopentene
Penta-n-tridecyl cyclopentene
Di-(2-octyl-1-dodecyl)cyclopentene
Tri-(2-octyl-1-dodecyl)cyclopentene
Tetra-(2-octyl-1-dodecyl)cyclopentene

Cyclopentadienes

Tri-dodecyl cyclopentadiene
Tetra-dodecyl cyclopentadiene
Penta-dodecyl cyclopentadiene
Penta-n-butyl cyclopentadiene
Penta-n-octyl cyclopentadiene
Penta-n-nonyl cyclopentadiene
Penta-n-decyl cyclopentadiene
Di-n-octyl, n-decyl cyclopentadiene
n-octyl, di-n-decyl cyclopentadiene
Trioctyl, n-decyl cyclopentadiene
Di-n-octyl, di-n-decyl cyclopentadiene
n-octyl, tri-n-decyl cyclopentadiene
Tri-n-tridecyl cyclopentadiene
Tetra-n-tridecyl cyclopentadiene
Penta-n-tridecyl cyclopentadiene
Di-(2-octyl-1-dodecyl)cyclopentadiene
Tri-(2-octyl-1-dodecyl)cyclopentadiene
Tetra-(2-octyl-1-dodecyl)cyclopentadiene
Di-n-octyl-Tri-n-decyl cyclopentadiene
Tri-n-octyl-Di-n-decyl cyclopentadiene
Methyl-n-octyl-n-decyl cyclopentadiene
Methyl-Di-n-octyl-n-decyl cyclopentadiene
Methyl-Tri-n-octyl-n-decyl cyclopentadiene
Methyl-n-octyl-di-n-decyl cyclopentadiene
Methyl-n-octyl-tri-n-decyl cyclopentadiene
Dimethyl-n-octyl-n-decyl cyclopentadiene
Dimethyl-di-n-octyl-n-decyl cyclopentadiene
Dimethyl-n-octyl-di-n-decyl cyclopentadiene
n-nonyl-n-decyl-n-undecyl cyclopentadiene
Di-n-nonyl-n-decyl-n-undecyl cyclopentadiene
n-nonyl-di-n-decyl-n-undecyl cyclopentadiene
n-nonyl-n-decyl-di-n-undecyl cyclopentadiene.

The hydrocarbyl substituted cyclopentadiene intermediates of the invention are prepared using a hydrocarbylating or phase transfer preparation method or an alcohol preparation method. In the phase transfer method, cyclopentadiene or substituted cyclopentadiene and an alkylating agent such as an alkyl halide or mixture of alkyl halides are added to a reaction vessel containing an alkaline aqueous solution and further containing a phase transfer catalytic agent. The alkylating agent is used in a molar excess depending on the amount of alkyl substitution desired. The preferred alkylating agent is an alkyl halide of the formula, $R_2Y$ wherein $R_2$ is as described above and Y is a leaving group, preferably Cl or Br, and the process is described herein with reference to this reaction. It is preferred that about 3 to 6 moles of alkyl halide should be used per mole of cyclopentadiene. The alkaline aqueous solution will comprise sodium hydroxide or potassium hydroxide in preferred embodiments. The mixture of cyclopentadiene, alkyl halide, catalyst and alkali is permitted to react in aqueous solution with vigorous stirring for a period of from about ½ to 10 hours. On completion of the reaction, and cessation of agitation, two phases will form, an organic phase and a water phase. The product will be contained in the organic phase and may be recovered by conventional methods as by separation of phases and recovery.

It is sometimes desirable to add an organic solvent or water or both to facilitate separation of the two phases. In a preferred procedure, the organic layer is removed and any excess alkyl halide and/or solvent removed to provide the alkylated cyclopentadiene which can be used for conversion to the cyclopentane without further purification. This is a single step reaction which provides good yields of the substituted cyclopentadiene.

In conducting the hydrocarbylation reaction by the phase transfer method, the preferred temperature range is from about $-20°$ to $120°$ C. with a residence time or reaction time of from ¼ hour up to 3 days. The molar ratio of alkyl halide to cyclopentadiene should range from about 1:1 up to about 20:1. The ratio of alkali metal hydroxide to cyclopentadiene reactant in this reaction may range from 1:1 up to 50:1.

Suitable phase transfer catalysts include n-alkyl ($C_{12}$–$C_{16}$) dimethylbenzylammonium chloride, sold commercially as Hyamine 3500, triethylbenzylammonium chloride, sold commercially as TEBAC, a mixture of methyl trialkyl ($C_8$–$C_{10}$) ammonium chlorides, sold commercially as Adogen ® 464, polyethylene glycols and polyethers.

In a separate method for preparation of the hydrocarbon-substituted cyclopentadienes, an alcohol or mixture of alcohols of the formula $R_2OH$ wherein $R_2$ is as described above, is combined with a basic catalyst such as an alkali metal hydroxide or alkoxide in a reaction vessel. The alcohol reactant or mixture of alcohols is a primary or secondary alcohol and is used in sufficient amounts to provide a molar excess of about 3 to 6 moles. It is preferred to use a mixture of alcohols as the reactant since alkylated compounds of different side chain length can be produced. The use of mixtures of alcohols to alkylate cyclopentadienes greatly enhances the utility of the process. In particular, properties of products produced by alkylation of cyclopentadienes with a mixture of two or more alcohols can be continuously and conveniently varied between those of the products produced by the separate alkylation of cyclopentadienes with each of the two pure alcohols. The cyclopentadiene or hydrocarbon-substituted cyclopentadiene is then added to the reaction vessel at room temperature or a temperature as high as the reflux temperature of the mixture, which would be at about the boiling temperature of the alcohol(s) being used. Alternatively, a portion of the cyclopentadiene may be mixed with the alcohol and alkali in the reactor and the remaining cyclopentadiene added to the reaction mixture over a period of time as the reaction proceeds. An inert solvent may also be included if necessary depending on the alcohol reactants. Further, the reaction may be carried out in a closed container so that higher temperatures in excess of 180°, and up to 260° C. can be reached using lower boiling alcohols. As the reaction proceeds, water will be produced and is removed as it is formed. This is an important feature of the invention since it appears to drive the reaction to completion and increase yields substantially. On completion of the reaction, the mixture is allowed to cool and then mixed with water or poured onto ice and two layers allowed to separate. The organic and aqueous layers are separated using an organic solvent to aid the separation if necessary. After removal of excess alcohol and any solvent from the organic layer, the polyalkyl cyclopentadiene is recovered.

In an alternative work-up procedure, the reaction mixture may be filtered. The alcohol may be separated by distillation before or after filtration.

It was unexpected that high yields of polyalkylated products from alcohols, including long chain alcohols, could be obtained from this reaction without the use of high pressure.

In conducting the hydrocarbylation by the alcohol method, minor side products may be formed. For example, the acid corresponding to the alcohol and a dimeric alcohol may also be formed. The careful exclusion of oxygen and careful adjustment of the alcohol to base ratios aid in suppression of the formation of these by-products. If secondary alcohols are used, the by-products are less significant.

The alcohol alkylation is preferably carried out in the temperature range of 180°–300° C. for a reaction time which may range from 10 minutes to 3 days. The mole ratio of alcohol to cyclopentadiene may range from 1:1 up to 50:1 and the ratio of alkali metal hydroxide or alkoxide to cyclopentadiene reactant may range from 0.1:1 up to 10:1.

The precursor cyclopentadienes to be reacted by the phase transfer method or alcohol method are preferably those set forth in Formula V above except that in such case, x can be 0, and x+z must be 0, 1, 2, 3, 4 or 5 in the phase transfer method, and x+z must be 0, 1, 2, 3 or 4 in the alcohol method. Also, no two hydrocarbon substituents can be germinal. For example the $R_1$ and/or $R_2$ hydrocarbyl groups could be added stepwise depending on the amount of hydrocarbylating agent used. The final products and precursor compounds as described are considered to be inclusive of all such compounds.

The cyclopentene intermediates of this invention are produced by partial or incomplete hydrogenation of the cyclopentadienes when preparing the cyclopentanes. This hydrogenation reaction if carried to completion will produce the cyclopentanes described above. However, incomplete hydrogenation will result in production of at least some cyclopentenes and usually a mixture of the hydrocarbon substituted cyclopentenes and cyclopentanes. Some starting cyclopentadienes which are not hydrogenated may also remain in the mixture. Thus, the hydrogenation reaction can produce a variety of mixtures of products as well as the cyclopentenes and the cyclopentanes of the invention.

The following examples are presented to illustrate the invention but the invention is not to be considered as limited thereto. In the examples and throughout the specification, parts are by weight unless otherwise indicated.

EXAMPLE 1

Preparation of Di(n-octyl)cyclopentadienes (Phase Transfer Method)

Cyclopentadiene (99 g, 1.5 moles), and n-octyl bromide (476 g, 3.2 moles), were added to a 5-liter reaction flask, containing an aqueous 56 percent potassium hydroxide solution (1950 ml, 30 moles KOH) and a catalytic amount of Adogen ® 464 (25 g), cooled in an ice bath. The mixture was stirred vigorously for 30 minutes in the ice bath, then the bath was removed. The mixture was stirred for an additional 3 hours, while warming to room temperature. The layers were separated, water and pentane being added to facilitate workup, and the organic phase was washed with water until neutral. The organic layer was dried over $MgSO_4$ and the pentane removed in vacuo, affording 372 g crude yield.

Gas chromatographic analysis provided the following analysis (86.5% total yield):

mono(n-octyl)cyclopentadienes 15.2%, 56.5 g, 0.317 moles (21.1% yield)
di(n-octyl)cyclopentadienes 75.7%, 281.6 g, 0.971 moles (64.7% yield);
tri(n-octyl)cyclopentadienes 1.1%, 4.1 g, 0.010 moles (0.6% yield).

EXAMPLE 2

Preparation of tri/tetra(n-decyl)cyclopentadienes (Phase Transfer Method)

Cyclopentadiene (23 g, 0.35 moles), and n-decyl bromide (300 g, 1.36 moles), were added to a 2-liter reaction flask containing an aqueous 56 percent potassium hydroxide solution (500 ml, 7.5 moles KOH) and a catalytic amount of Adogen ® 464 (13 g), in a water bath at room temperature. The mixture was vigorously stirred for one hour then heated, with continuing stirring for 4½ hours at 100° C. After cooling, the layers were separated, water and heptane added to facilitate workup, and the organic phase was washed with water until neutral. The organic phase was dried over $MgSO_4$ and the solvent removed in vacuo, affording 247 g crude yield. Unreacted n-decyl bromide (40 g, 0.18 mole) was distilled off to give a pot residue (200 g) of product.

Gas chromatographic analysis provided the following analysis (98.6% total yield):
di(n-decyl)ether 3.4%, 6.8 g, 0.023 moles;
di(n-decyl)cyclopentadienes 0.8%, 1.6 g, 0.005 moles (1.4% yield); tri(n-decyl)cyclopentadienes 41.2%, 82.4 g, 0.170 moles (48.6% yield);
tetra(n-decyl)cyclopentadienes 53.3%, 106.6 g, 0.170 moles (48.6% yield).

EXAMPLE 3

Preparation of Isodecylcyclopentanes (Alcohol method)

Isodecanol (420 g, 2.65 moles) and solid potassium hydroxide (87%, 10.3 g, 0.16 moles KOH) were mixed in a 1-liter reaction flask fitted with a mechanical stirrer, a dropping funnel, a Dean-Stark trap with condenser, a thermometer and a serum capped sampling port. Prior to heating, a portion of the dicyclopentadiene (6.6 g, 0.05 moles) was added to the reaction mixture. The flask was then heated to 200° C. After water began collecting in the Dean-Stark trap, the remaining dicyclopentadiene (28.4 g, 0.22 moles) was added dropwise over a 1.5 hour period. The reaction mixture was heated for 4 hours after the completion of the dicyclopentadiene addition. The temperature rose to 245° C. over the course of the reaction. After cooling, the reaction mixture was poured into water. Hexane was added to facilitate workup. The layers were separated. The aqueous layer was saved for further workup. The organic phase was washed with water until neutral. The organics were dried over $MgSO_4$ and the solvent removed in vacuo. The organic concentrate was carried through the hydrogenation affording 387 g.

Gas chromatographic analysis provided the following analysis (80% total yield):
isodecanol 25.4%, 98.3 g, 0.621 moles;
isoeicosanol 2.9%, 11.2 g, 0.0380 moles;
tri(isodecyl)cyclopentanes 7.0%, 27.1 g, 0.056 moles (11% yield);
tetra(isodecyl)cyclopentanes 48.1%, 186.1 g, 0.297 moles (56% yield);
penta(isodecyl) cyclopentanes 13.0%, 50.3 g, 0.066 moles (13% yield).

The aqueous layer was acidified with hydrochloric acid and extracted with ether. The layers were separated and the organic layer washed with water until neutral. The organics were dried over $MgSO_4$ and the solvent removed in vacuo, affording isodecanoic acid (23.4 g, 0.136 moles). Of the 2.65 moles of isodecanol used, 2.52 moles (95%) are accounted for.

EXAMPLE 4

Hydrogenation of tri(n-decyl)cyclopentadienes

A 4-liter autoclave was charged with the crude alkylcyclopentadienes (159 g; di(n-decyl)cyclopentadienes, 34.7 g, 21.8%; tri(n-decyl)cyclopentadienes, 117.2 g, 73.7%; and tetra(n-decyl)cyclopentadienes 2.2 g, 1.4%), (prepared as in Example 2) 10% palladium on activated carbon (4 gms), and heptane (500 ml) to facilitate stirring. The vessel was pressurized to 500 psi of hydrogen and heated at 125° C. for 19 hours with stirring. After cooling, the vessel pressure was 350 psi. The catalyst was filtered and the solvent removed in vacuo affording 150 g of clear colorless oil with a bromine number of zero.

EXAMPLE 5

Using the procedures of Examples 1, 2 and 3, the cyclopentadiene derivatives set forth in the following Table 1 were prepared. The table indicates the preparative method used.

TABLE 1

CYCLOPENTADIENE DERIVATIVE

| | | | | x = | | | | |
|---|---|---|---|---|---|---|---|---|
| $R_2$ | Formula | Class[a] | Method[b] | 2 | 3 | 4 | 5 | 6 |
| n-butyl | $C_4H_9$ | 1° | P | x | x | x | x | x |
| n-hexyl | $C_6H_{13}$ | 1° | P | x | x | x | x | x |
| n-octyl | $C_8H_{17}$ | 1° | P, A | x | x | x | x | |
| n-decyl | $C_{10}H_{21}$ | 1° | P, A | x | x | x | x | |
| n-dodecyl | $C_{12}H_{25}$ | 1° | P, A | x | x | x | x | |
| n-tetradecyl | $C_{14}H_{29}$ | 1° | P | x | x | x | | |
| isodecyl | $C_{10}H_{21}$ | 1° | A | x | x | x | x | |
| isotridecyl | $C_{13}H_{27}$ | 1° | A | x | x | x | x | |
| 2-ethyl-1-hexyl | $C_8H_{17}$ | 1° | P, A | x | x | x | | |
| 2-octyl-1-dodecyl | $C_{20}H_{41}$ | 1° | A | x | x | | | |
| 2-decyl-1-tetradecyl | $C_{24}H_{49}$ | 1° | A | x | x | | | |

TABLE 1-continued
CYCLOPENTADIENE DERIVATIVE

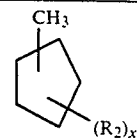

| R$_2$ | Formula | Class$^a$ | Method$^b$ | x = 2 | 3 | 4 | 5 | 6 |
|---|---|---|---|---|---|---|---|---|
| 2-octyl | C$_8$H$_{17}$ | 2$^s$ | P, A | x | x | | | |
| t-butyl | C$_4$H$_9$ | 3$^t$ | P | x | x | | | |

$^a$ 1$^c$ = primary alkyl; 2$^s$ = secondary alkyl; 3$^t$ = tertiary alkyl
$^b$ P = Phase Transfer method; A = Alcohol method

EXAMPLE 6

Using the procedures of Examples 1, 2 and 3, the methylcyclopentadienes set forth in the following Table 2 were prepared. The preparative method is indicated.

TABLE 2
METHYLCYCLOPENTADIENE

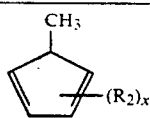

| R$_2$ | Formula | Class$^a$ | Method$^b$ | x = 2 | 3 | 4 | 5 |
|---|---|---|---|---|---|---|---|
| n-octyl | C$_8$H$_{17}$ | 1$^c$ | A | x | x | x | |
| n-decyl | C$_{10}$H$_{21}$ | 1$^c$ | A, P | x | x | x | |
| n-dodecyl | C$_{12}$H$_{25}$ | 1$^c$ | A | x | x | x | |
| isodecyl | C$_{10}$H$_{21}$ | 1$^c$ | A | x | x | x | |

$^a$ 1$^c$ = primary alkyl
$^b$ P = Phase Transfer method; A = Alcohol method

EXAMPLE 7

Using the hydrogenation procedures of Example 4, the alkyl substituted cyclopentanes of Table 3 were prepared. The column indicating "Class" designates a straight or branch chained substituent.

TABLE 3
CYCLOPENTANE DERIVATIVES

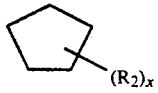

| R$_2$ | Formula | Class$^a$ | x = 2 | 3 | 4 | 5 |
|---|---|---|---|---|---|---|
| n-octyl | C$_8$H$_{17}$ | 1$^c$ | x | x | x | x |
| n-decyl | C$_{10}$H$_{21}$ | 1$^c$ | x | x | x | x |
| n-dodecyl | C$_{12}$H$_{25}$ | 1$^c$ | x | x | x | x |
| isodecyl | C$_{10}$H$_{21}$ | 1$^c$ | x | x | x | x |
| isotridecyl | C$_{13}$H$_{27}$ | 1$^c$ | x | x | x | x |
| 2-ethyl-1-hexyl | C$_8$H$_{17}$ | 1$^c$ | x | x | x | |
| 2-octyl-1-dodecyl | C$_{20}$H$_{41}$ | 1$^c$ | x | x | | |
| 2-decyl-1-tetradecyl | C$_{24}$H$_{49}$ | 1$^c$ | x | x | | |
| 2-octyl | C$_8$H$_{17}$ | 2$^s$ | x | x | | |

$^a$ 1$^c$ = primary alcohol; 2$^s$ = secondary alcohol

EXAMPLE 8

Using the hydrogenation procedures of Example 4, the substituted methylcyclopentanes of Table 4 were prepared. The column indicating "Class" designates a straight or branch chained substituent.

TABLE 4
METHYLCYCLOPENTANE DERIVATIVES

| R$_2$ | FORMULA | CLASS | x = 2 | 3 | 4 |
|---|---|---|---|---|---|
| n-octyl | C$_8$H$_{17}$ | 1$^c$ | x | x | x |
| n-decyl | C$_{10}$H$_{21}$ | 1$^c$ | x | x | x |
| n-dodecyl | C$_{12}$H$_{25}$ | 1$^c$ | x | x | x |
| isodecyl | C$_{10}$H$_{21}$ | 1$^c$ | x | x | x |

EXAMPLE 9—CHEMICAL IDENTIFICATION

Chemical characterization of alkylcyclopentadienes and alkylcyclopentanes was by infrared spectroscopy (IR), nuclear magnetic resonance spectrometry (NMR) and gas chromatography (GC), especially in conjunction with mass spectrometry (GC-MS). A few examples were meticulously examined and structures of products determined and then quantitative analysis and further identification was made by analogy to these carefully characterized samples.

Interpretation of Spectroscopic Data

Mass Spectrometry

Alkylcyclopentadienes (see Table 5 following)—A detailed analysis of n-butyl cyclopentadienes showed that the parent peak was prominent enough to be recognizable. Common fragments were P-43 (minus n-propyl), P-57 (minus n-butyl), P-98 (minus propene and butene), P-99 (minus n-propyl and n-butene) and 57 (n-butyl). Other cyclopentadienes also gave parent peaks prominent enough to allow assignment to be made on that basis alone.

Alkylcyclopentanes—Mass spectra are very similar to other saturated hydrocarbons except that the parent is C$_n$H$_{2n}$.

Infrared Spectroscopy

Alkylcyclopentanes (See Table 6 following)—The IR spectra are indistinguishable from other saturated hydrocarbons with alkyl components; e.g., hydrogenated 1-decene oligomers. Bands are at 2960 cm$^{-1}$, 2850 cm$^{-1}$ (H-C(sp$^3$) stretch); 1460 cm$^{-1}$, 1375 cm$^{-1}$, (H-C(sp$^3$) bend) and 720 cm$^{-1}$ (—(CH$_2$)$_x$—rock, x>4).

Alkylcyclopentadienes (See Table 6)—In addition to the bands found in the alkylcyclopentanes, bands for unsaturation are found at 3050 cm$^{-1}$ (H-C(sp$^2$) stretch), 1650 and 1620 (C=C stretch), 970 and 890 (H-C(sp$^2$) bend).

Nuclear Magnetic Resonance Spectrometry

Alkylcyclopentanes—Both $^1$H and $^{13}$C NMR Spectra are dominated by n-alkyl resonances: (1) $^1$H NMR, CH$_3$ at 0.9 ppm, CH$_2$ at 1.3 ppm, CH at 1.5; (2) $^{13}$C NMR, CH$_3$— 14.2 ppm, CH$_2$'s at 22.8 ppm, 29.7 ppm, 32.0 ppm and CH's clustered about 40 ppm.

Alkylcyclopentadienes—In addition to the resonance of alkylcyclopentanes due to the alkyl groups, unsaturation leads to resonances at 5.80 and 6.20 ppm in the $^1$H spectrum for protons on sp$^2$ carbon and 2.35 and 2.8 for allylic and bis-allylic CH$_2$'s respectively. Similarly, resonances due to unsaturation are observed in the 150.0 to 110.00 ppm region for sp$^2$ carbons and 45.0 to 35.0 ppm region for allylic carbons in the $^{13}C$ spectra of alkylcyclopentadienes.

temperature properties of the indicated alkylcyclopentanes.

TABLE 5

Mass Spectral Data for Alkyl Cyclopentadienes
GC - Mass Spec of $C_5(R_2)_xH_{6-x}$, $R_2$ = n-butyl

| X | Retention Time (Minutes) | P (Parent) $M^-$ | P-43 $-C_3H_7$ | P-56 $-C_4H_8$ | P-57 $-C_4H_9$ | P-71 $-C_5H_{11}$ | P-85 $-C_6H_{13}$ | P-88 $-C_7H_{14}$ | P-99 $-C_7H_{14}$ | 57 $C_4H_9$ |
|---|---|---|---|---|---|---|---|---|---|---|
| 2 | 20.4 | 24 | 45 | 0 | 42 | 24 | 95 | 63 | 100 | 40 |
| 3 | 29.4 | 18 | 53 | 55 | 18 | 53 | 19 | 40 | 100 | 60 |
| 3 | 29.5 | 18 | 33 | 3 | 16 | 62 | 17 | 27 | 100 | 53 |
| 3 | 32.1 | 27 | 100 | 2 | 12 | 10 | 42 | 40 | 42 | 24 |
| 4 | 35.8 | 9 | 52 | 3 | 10 | 0 | 8 | 29 | 27 | 100 |
| 4 | 36.1 | 22 | 100 | 12 | 23 | 2 | 12 | 47 | 50 | 88 |
| 4 | 36.5 | 25 | 100 | 10 | 25 | 2 | 12 | 47 | 38 | 86 |
| 4 | 37.2 | 17 | 22 | 88 | 18 | 1 | 7 | 47 | 100 | 62 |
| 4 | 37.9 | 30 | 100 | 8 | 20 | 3 | 12 | 35 | 42 | 56 |
| 4 | 38.3 | 7 | <1 | 18 | 100 | 0 | 1 | <1 | 3 | 16 |
| 5 | 40.8 | 32 | 79 | 23 | 19 | 0 | 5 | 14 | 38 | 100 |
| 5 | 41.4 | 45 | 100 | 23 | 19 | 1 | 6 | 27 | 35 | 67 |
| 5 | 42.2 | 5 | <1 | 26 | 100 | 0 | 0 | 2 | 2 | 17 |
| 6 | 45.5 | 100 | 89 | 32 | 30 | 0 | 2 | 10 | 38 | 37 |

TABLE 6

Infrared Spectra of Representative Alkylcyclopentadienes and Alkylcyclopentanes
Di(n-decyl)cyclopentadienes and Di(n-decyl)cyclopentanes.

| Frequency, $\nu$ | | |
|---|---|---|
| ⌖(n-C₁₀H₂₁)₂ | ⌖(n-C₁₀H₂₁)₂ | Assignment |
| 3044 cm⁻¹ | | sp² C—H stretch |
| 2960 | 2960 | sp³ C—H stretch |
| 2850 | 2850 | sp³ C—H stretch |
| 1653 | | c=c stretch |
| 1622 | | c=c stretch |
| 1560 | | c=c stretch |
| 1465 | 1465 | CH₂ bending |
| 1375 | 1375 | CH₃ bending |
| 968 | | sp² C—H bend |
| 891 | | sp² C—H bend |
| 721 | 721 | —(CH₂)ₓ— x > 4, rocking |

EXAMPLE 10

To evaluate the alkyl cyclopentanes for lubricating properties, tests were carried out to measure physical properties which are relevant to use as a synthetic lubricant. Set forth in the following Table 7 are specific gravity values of the indicated cyclopentanes, in Table 8 are set forth refractive index values of the indicated cyclopentanes, in Table 9 are set forth viscometric properties of the indicated alkylcyclopentanes; in Table 10 are low temperature properties of the indicated alkylcyclopentanes; and set forth in Table 11 are high

TABLE 7

Specific Gravity of Representative Alkylcyclopentanes

| | | | X = | | | |
|---|---|---|---|---|---|---|
| Sample # | R₁ | R₂ | 2 | 3 | 4 | 5 | S.G. |
| 1 | H | (n-decyl) | — | 100% | — | — | 0.8368 |
| 2 | H | (n-octyl) | — | — | 100% | — | 0.8368 |
| 3 | H | (n-decyl) | — | 20% | 70% | 10% | 0.8430 |
| 4 | H | (n-decyl) | — | — | 67% | 33% | 0.8450 |
| 5 | H | (n-dodecyl) | — | 40% | 60% | — | 0.8509 |

TABLE 8

Refractive Indexes of Representative Alkylcyclopentanes

| Sample # | R₁ | R₂ | X = 2 | 3 | 4 | 5 | $n_D^{25°\,C.}$ |
|---|---|---|---|---|---|---|---|
| 1 | H | n-octyl | — | 100% | — | — | 1.4573 |
| 2 | H | n-decyl | — | 100% | — | — | 1.4604 |
| 3 | H/Me=1/1 | n-decyl | — | 100% | — | — | 1.4612 |
| 4 | H | n-octyl | — | — | 100% | — | 1.4612 |
| 5 | Me | n-octyl | — | 40% | 60% | — | 1.4630 |
| 6 | H | n-decyl | — | 30% | 65% | 5% | 1.4636 |
| 7 | H | n-decyl | — | — | 67% | 33% | 1.4654 |
| 8 | H | n-dodecyl | — | 40% | 60% | — | 1.4647 |
| 9 | H | isodecyl | | | | | 1.4672 |

TABLE 9

Viscometric Properties of Representative Alkylcyclopentanes

| | | | X = | | | | Viscosity | | | | |
|---|---|---|---|---|---|---|---|---|---|---|---|
| Sample # | R₁ | R₂ | 2 | 3 | 4 | 5 | 100° C. (cSt)$^a$ | 40° C. (cSt)$^a$ | 0° C. (cP)$^b$ | −40° C. (cP)$^b$ | Viscosity Index |
| 1 | H | n-octyl | 100% | — | — | — | 2.18 | 6.49 | | | 158 |
| 2 | H | n-decyl | 100% | — | — | — | 3.03 | 10.37 | | | 161 |
| 3 | H | n-dodecyl | 100% | — | — | — | 4.13 | 15.64 | | | 178 |
| 4 | H | n-octyl | — | 100% | — | — | 3.68 | 15.58 | — | 1676 | 124 |
| 5 | H | n-decyl | — | 100% | — | — | 5.15 | 23.99 | | | 151 |

TABLE 9-continued
Viscometric Properties of Representative Alkylcyclopentanes

| Sample # | $R_1$ | $R_2$ | X = 2 | X = 3 | X = 4 | X = 5 | 100° C. (cSt)[a] | 40° C. (cSt)[a] | 0° C. (cP)[b] | −40° C. (cP)[b] | Viscosity Index |
|---|---|---|---|---|---|---|---|---|---|---|---|
| 6 | Me | n-decyl | — | 100% | — | — | 5.82 | 29.64 | 247 | 6,886 | 143 |
| 7 | H/Me = 1/1 | n-decyl | — | 100% | — | — | 5.60 | 27.82 | 242 | 5,800 | 145 |
| 8 | H | n-dodecyl | — | 100% | — | — | 6.99 | 35.26 | | | 150 |
| 9 | H | n-octyl | — | — | 100% | — | 5.99 | 33.43 | 363 | 15,386 | 125 |
| 10 | H | n-decyl | — | — | 100% | — | 7.99 | 46.70 | 602 | 14,958 | 143 |
| 11 | H | isodecyl | — | — | X | — | 11.68 | 119.60 | 2,584 | 556,000 | 83 |
| 12 | H | isotridecyl | — | — | X | — | 20.09 | 310.22 | 12,700 | solid | 71 |
| 13 | H | 2-octyldodecyl | 15% | 85% | — | — | 15.10 | 114.97 | 1,500 | 224,000 | 136 |
| 14 | H | 2-decyltetradecyl | 40% | 60% | — | — | 16.34 | 118.51 | | | 148 |
| 15 | H | n-dodecyl | — | — | 50% | 50% | 11.91 | 83.19 | | | 153 |

[a]ASTM D445
[b]ASTM D3829
[c]ASTM D2270

TABLE 10
Low Temperature Properties of Representative Alkylcyclopentanes

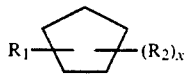

| Sample # | $R_1$ | $R_2$ | X = 2 | X = 3 | X = 4 | X = 5 | MRV[a],cp −30° C. | CCS[b],cp −25° C. | Pour[c] Point, °F. |
|---|---|---|---|---|---|---|---|---|---|
| 1 | H | n-octyl | 100% | — | — | — | | | −10 |
| 2 | H | n-decyl | 100% | — | — | — | | | +40 |
| 3 | H | n-dodecyl | 100% | — | — | — | | | +70 |
| 4 | H | n-octyl | — | 100% | — | — | 720 | <500 | <−70° |
| 5 | H | n-decyl | — | 100% | — | — | | | −20 |
| 6 | H | n-dodecyl | — | 100% | — | — | | | +15 |
| 7 | H | n-octyl | — | — | 100% | — | 3,662 | 1,640 | <−55 |
| 8 | H | n-decyl | — | — | 100% | — | 4,498 | 2,385 | <−75 |
| 9 | H | n-dodecyl | — | 40% | 60% | — | | | +5 |
| 10 | H | n-decyl | — | 20% | 70% | 10% | 3,375 | 2,263 | <−65 |
| 11 | Me | n-octyl | — | 40% | 60% | — | 2,171 | 1,200 | <−60° |
| 12 | Me | n-decyl | — | 67% | 33% | — | 2,549 | 1,850 | <−50° |
| 13 | H | n-decyl | — | — | 67% | 33% | 5,743 | 3,500 | <−50° |
| 14 | Me | n-decyl | — | 100% | — | — | 2,931 | 1,350 | <−60° |
| 15 | H/Me = 1:1 | n-decyl | — | 100% | — | — | 2,681 | 1,186 | <−50° |
| 16 | H | 2-ethylhexyl | — | 95% | 5% | — | | | <−55 |
| 17 | H | 2-octyl | 15% | 85% | — | — | | | <−65 |
| 18 | H | isodecyl | — | — | X | — | 103,000 | >15,000 | −30 |
| 19 | H | isotridecyl | — | — | X | — | 369,000 | solid | −15 |
| 20 | H | 2-octyldodecyl | 15% | 85% | — | — | 20,500 | 11,700 | −60 |

[a]MRV = Borderline pumping test by minirotary viscometer (ASTM D3829)
[b]CCS = Cold cranking simulator (ASTM D2062)
[c]Pour Point (ASTM D97)

TABLE 11
High Temperature Properties of Alkylcyclopentanes

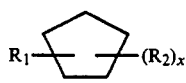

| Sample # | $R_1$ | $R_2$ | X = 2 | X = 3 | X = 4 | X = 5 | Flash[a] Point, °F. | Fire[b] Point, °F. | Evaporation[c] Loss, % |
|---|---|---|---|---|---|---|---|---|---|
| 1 | H | n-decyl | — | 100% | — | — | 500 | 565 | 0.5 |
| 2 | H | n-decyl | — | 45% | 50% | 5% | 520 | 580 | — |
| 3 | H | n-decyl | — | — | 67% | 33% | 550 | 620 | — |
| 4 | H | n-dodecyl | — | 40% | 60% | — | 560 | 625 | 0.1 |

[a]ASTM D92
[b]ASTM D92
[c]ASTM D972, 400° F., 6.5 hr., 2L/min $N_2$

EXAMPLE 11

To evaluate the hydrocarbon substituted cyclopentadienes for lubricating properties, tests were carried out to measure physical properties which are relevant to use as a synthetic lubricant. Set forth in the following Table 12 are viscosity and pour point properties of the identical alkyl substituted cyclopentadienes. In the cyclopentadienes tested, $R_1$ is hydrogen, x is 2 to 6 and $R_2$ is as indicated.

TABLE 12

Viscometric Properties of Alkylcyclopentadienes

| Sample | $R_2=$ | Vis (100° C.), cSt[a] | Vis (40° C.), cSt[a] | Viscosity[b] Index | Pour[c] Point, °F. |
|---|---|---|---|---|---|
| 1 | n-Butyl | 2.65 | 12.69 | −3 | < −60 |
| 2 | n-Decyl | 5.00 | 22.35 | 157 | 0 |
| 3 | n-octyl/n-decyl | 6.06 | 31.04 | 146 | −5 |
| 4 | 2-octyl-1-dodecyl | 12.78 | 93.38 | 133 | −50 |

[a]ASTM D445
[b]ASTM D2270
[c]ASTM D97

EXAMPLE 12

Preparation of Alkylcyclopentenes

The tri- and tetrasubstituted alkyl cyclopentadienes (a mixture of n-octyl and n-decyl alkyl groups) were mildly hydrogenated over PD/C at ambient temeprature. The alkylcyclopentadienes (350 g), 10% PD/C catalyst (3.0 g) and light hydrocarbon solvent (500 mL) were placed in a 4-liter autoclave. After purging with hydrogen, the system was pressurized to 600 psig hydrogen. The system was stirred for 8 hours at room temperature after which time the pressure dropped to 510 psig. The solution was filtered through a bed of Celite to remove the catalyst and the solvent was removed in vacuo to afford 347 g of a yellowish oil.

Spectroscopic Characterization of Alkylcyclopentenes

Alkyl cyclopentenes produced by mild hydrogenation can be distinguished spectroscopically from the alkylcyclipentanes and alkylcyclopentadienes in the following ways:

1. Ultraviolet Spectra—Alkylcyclopentadienes are characterized by an intense absorption at about 260 nm. This band disappears upon hydrogenation to alkylcyclopentanes, and another band, near 220 nm, appears. Upon further hydrogenation of the product alkylcyclopentenes, the 220 nm band disappears as the alkylcyclopentenes are converted into the UV transparent alkylcyclopentanes.

2. $^1$H Nuclear Magnetic Response Spectra—Alkylcyclopentadienes shows resonances for the doubly allylic ring $CH_2$'s and CHR's at 2.7 to 2.8 ppm downfield of the tetramethylsilane. Upon hydrogenation, these resonances disappear and additional resonances in the 1.6 to 2.0 ppm region characteristic of singly allylic $CH_2$'s and CHR's develop. Upon further hydrogenation of the alkylcyclopentenes, the intensity of resonances in the 1.6 to 2.0 ppm region of the spectrum decrease as the alkylcyclopentenes are converted into alkylcyclopentanes.

Figure 2:
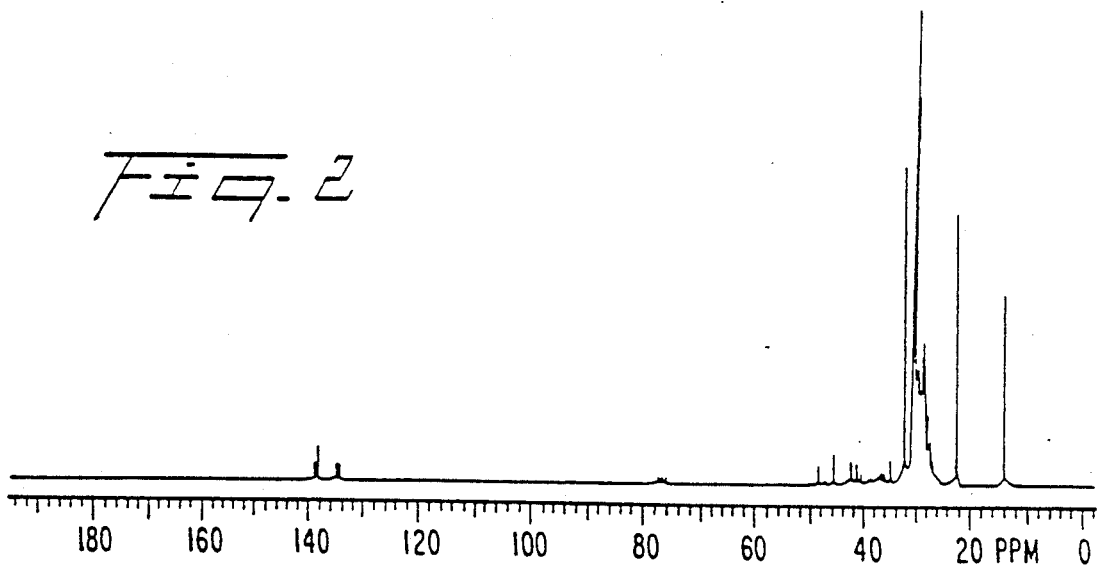
FIG. 2 is the $^{13}C$ nmr spectrum of alkylcyclopentene.
Figure 3:
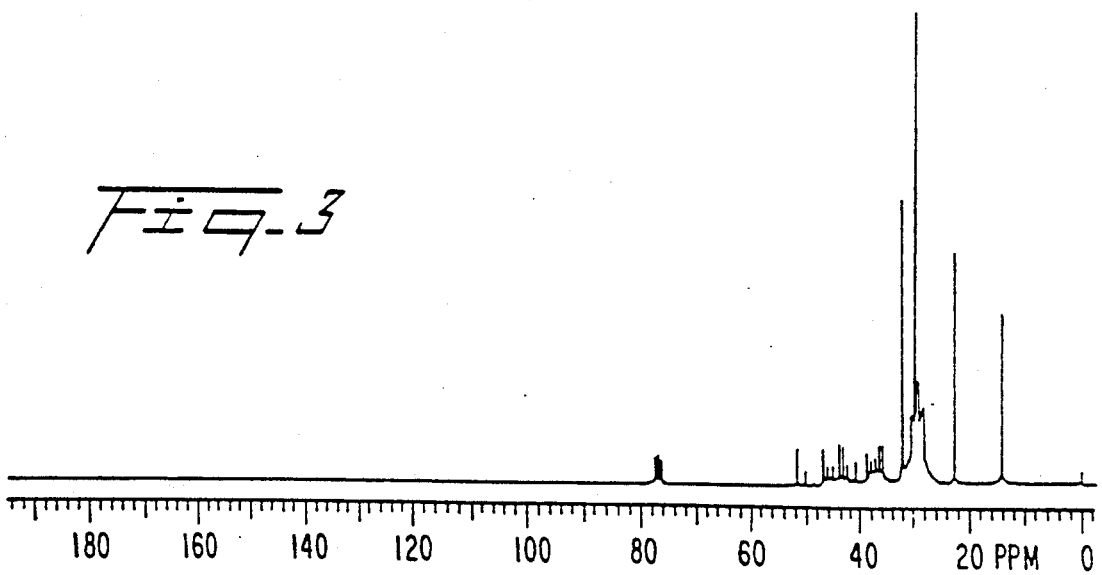
FIG. 3 is the $^{13}C$ nmr spectrum of alkylcyclopentane.

3. $^{13}$C Nuclear Magnetic Response Spectra—In the region of the spectrum 110 to 160 ppm downfield from tetramethylsilane, a multitude of resonances can be observed for alkylcyclopentadienes. Upon hydrogenation, these resonances disappear and new resonances in the 130 to 145 ppm region of the spectrum characteristic of the alkylcyclopentenes appear. Upon further hydrogenation of the alkylcyclopentenes, the resonances in the 130 to 145 region of the spectrum disappear and the spectrum becomes transparent from 55 to 200 ppm, as one would predict for a full saturated material. FIGS. 1 to 3 are the $^{13}$C nmr spectra of alkylcyclopentadiene, alkylcyclopentene, and alkylcyclopentane respectively.

TABLE 13

Physical Properties of Some Alkylcyclopentadienes[a], Alkylcyclopentenes and Alkylcyclopentanes derived from them.

| | VISCOSITIES | | Viscosity Index | Pour Point, deg F. |
|---|---|---|---|---|
| | 100C, cSt | 40C, cSt | | |
| Alkylcyclopentadiene 1 | 5.02 | 23.46 | 147 | −60 |
| Alkylcyclopentene 1 | 5.10 | 24.29 | 144 | < −65 |
| Alkylcyclopentane 1 | 5.27 | 25.66 | 143 | < −65 |
| Alkylcyclopentadiene 2 | 6.06 | 31.04 | 146 | −5 |
| Alkylcyclopentene 2 | 6.09 | 31.39 | 145 | −50 |
| Alkylcyclopentane 2 | 6.33 | 34.17 | 138 | < −65 |
| Alkylcyclopentadiene 3 | 4.99 | 35.30 | 41 | −71 |
| Alkylcyclopentene 3 | 4.93 | 34.69 | 39 | −71 |
| Alkylcyclopentane 3 | 4.96 | 35.14 | 39 | −71 |

[a]Alkylcyclopentadienes 1 and 2 are different products prepared by the alkylation of cyclopentadiene with a mixture of n-octanol and n-decanol: Alkylcyclopentadiene 3 was prepared by alkylation of cyclopentadiene with 2-ethylhexanol.

The synthetic lubricating compositions of the present invention are used as lubricants by blending with one or more additives conventionally used with lubricating oil obtained from natural sources or other types of synthetic lubricating oil. Thus, there may be included within the synthetic lubricating oil of this invention from 0.01 up to about 40% by weight of conventional pour point depressants, viscosity index improvers, dispersants, load carrying agents, rust inhibitors, and antioxidants, as well as mixtures of such conventional additives. It will be understood that the synthetic lubricants of this invention will be mixed with the number of additives and amounts to provide good performance, particularly when used in internal combustion engines. Particular additives which may be used include polymethacrylates which are well known as pour point depressants and viscosity index improvers such as hydrogenated diolefin-lower alkyl acrylate or methacrylate copolymers. Other additives which may be blended with the lubricants of the invention include zinc dialkyl dithiophosphates, phenates, sulfonates, non-ionic dispersants, such as alkyl succinimides or Mannich bases of phenols, polyacrylate and methacrylate pour point depressants, and olefin copolymer or polyacrylate viscosity index improvers, or any other effective motor oil additives.

The synthetic lubricating oil of this invention may be blended in amount ranging from about 5% to 95% with a lubricant obtained from natural sources such as a refined paraffin-type base oil, a refined napthenictype base oil, asphaltic or mixed base crude and/or mixtures thereof. The viscosity of such oils may vary over a wide range such as from 70 SUS at 100° F. to 300 SUS at 210° F. and the boiling point of these oils may vary over a wide range as from 300°–750° F.

The synthetic lubricants of the present invention may also be blended with other synthetic lubricating oils such as those obtained by polymerization of lower molecular weight alkenes, as well as esters, phosphates and silicon-based lubricants. The blends with other synthetic lubricants will range from 5 to 95%. Mixtures of one or more other natural or synthetic lubricants may also be employed in the same proportions.

The following examples illustrate such mixtures and blends.

EXAMPLE 13

Engine oils are prepared by mixing:
1. an alkylcyclopentane,
2. a commercially available ester, such as Emery 2971,
3. a commercial detergent-inhibitor additive, such as Lubrizol 7608,
4. a commercial viscosity index improver, such as Texaco TLA 656,
5. a commercial phenolic antioxidant, such as Ethyl 728.

A typical formulation is shown in Table 14.

TABLE 14

Engine Oil made with Alkylcyclopentane Base Oil

| | % by weight |
|---|---|
| Formulation | |
| Alkylcyclopentane* | 57.3 |
| Emery 2971 | 24.0 |
| Lubrizol 7608 | 11.5 |
| TLA 656 | 7.0 |
| Ethyl 728 | 0.2 |
| Properties | |
| Viscosity, 100° C. | 10.99 cSt |
| Viscosity Index | 171 |
| Cold Cranking Simulator Viscosity, −25° C. | 2250 cP |
| SAE Grade | 5W-30 |

*Prepared from cyclopentadiene and Ethyl Corporation's EPAL 810, a commercially available mixture of n-octanol and n-decanol, by the method described in this disclosure. Properties of this particular base oil are Viscosity (100° C.) = 5.23 cSt; Viscosity Index = 134.

EXAMPLE 14

A proprietary engine test was carried out on three oils:
1. The 5W-30 motor oil based on alkylcyclopentane base oil described in Example 13,
2. a commercially available, fully synthetic, PAO/ester based, 5W-30 motor oil,
3. a commercially available, mineral oil based, 5W-30 motor oil.

The results are summarized in Table 15.

TABLE 15

Results of Engine Tests on 5W-30 Motor Oils

| | Oil of Table 14 | Commercial Synthetic | Commercial Mineral Oil |
|---|---|---|---|
| % Viscosity Increase at 70 hrs. | 6 | 27 | 590 |
| Rocker Arm Sludge* | 9.50 | 9.65 | 9.54 |
| Piston Skirt Varnish* | 8.3 | 8.6 | 8.0 |
| Oil Ring Land* Face Deposits | 6.88 | 6.84 | 5.14 |
| Oil Consumption, lbs. | 1.12 | 1.26 | 4.62 |

*Rating, maximum merit score of 10.

EXAMPLE 15

Engine oils were prepared by mixing:
1. an alkylcyclopentane,
2. commercial neutral mineral oils,
3. a commercial detergent-inhibitor additive, such as Lubrizol 7608,
4. a commercial viscosity index improver, such as Texaco TLA 656,
5. a commercial pour point depressant, such as Acryloid 154-70.

A typical formulation is shown in Table 16.

TABLE 16

Engine Oil Made with Alkylcyclopentane and Mineral Oil

| | % by weight |
|---|---|
| Formulation | |
| Alkylcyclopentane* | 25.8 |
| Mineral Oil (100 Neutral) | 42.7 |
| Mineral Oil (300 Neutral) | 11.8 |
| Lubrizol 7608 | 11.5 |
| TLA 656 | 8.0 |
| Acryloid 154-70 | 0.2 |
| Properties | |
| Viscosity, 100° C. | 11.55 cSt |
| Viscosity Index | 157 |
| Cold Cranking Simulator Viscosity, −25° C. | 3400 cP |
| Pour Point | −30° F. |
| SAE Grade | 5W-30 |

*Same base oil as that in Example 13 (see Table 14).

The application has been described with reference to certain preferred embodiments. However, as obvious variations thereon will become apparent to those skilled in the art, the invention is not to be considered as limited thereto.

We claim:

1. A synthetic lubricating composition comprising:
   (A) A synthetic lubricant comprising:
      (1) a hydrocarbyl substituted cyclopentane;
      (2) a hydrocarbyl substituted cyclopentadiene;
      (3) a hydrocarbyl substituted cyclopentene; or
      (4) mixtures in any proportions of (1), (2), and (3);
   in admixture with
   (B) a natural lubricant or a synthetic lubricant other than a member of (A); and
   (C) an effective amount of at least one lubricating oil additive selected from the group consisting of pour point depressants, viscosity index improvers, dispersants, load carrying agents, rust inhibitors, antioxidants, and mixtures thereof.

2. A composition according to claim 1 wherein the composition contains 5 to 95 wt. % of (A) and 95 to 5 wt. % of (B).

3. A composition according to claim 1 wherein the natural lubricant is a mineral oil.

4. A composition according to claim 1 wherein the synthetic lubricant is a poly-alpha-olefin, ester, polyol ester, or mixture thereof.

5. A lubricating composition according to claim 1 wherein the synthetic lubricant of (A) is cyclopentane substituted by at least two hydrocarbyl groups having 4 to 36 carbon atoms.

6. A synthetic lubricating composition according to claim 5 whererin the synthetic lubricant component (A) comprises at least one cyclopentane of the following formula:

wherein each $R_1$ is individually and independently selected from an alkyl groups of 1 to 4 carbons, each $R_2$ is individually and independently selected from straight or branch chained hydrocarbyl groups containing from 4 to 36 carbon atoms, z is 0, 1, 2 or 3, and x is an integer ranging from 2 to 6, and $x+z$ cannot be greater than 6.

7. A lubricating composition according to claim 1 wherein the synthetic lubricant of (A) is cyclopentadiene substituted by at least two hydrocarbyl groups having 4 to 36 carbon atoms.

8. A synthetic lubricating composition according to claim 7 wherein the synthetic lubricant (A) comprises at least one cyclopentadiene of the following formula:

wherein each $R_1$ is individually and independently selected from alkyl groups of 1 to 4 carbon atoms, each $R_2$ is individually and independently selected from straight or branch chained hydrocarbyl groups having 4 to 36 carbon atoms, z is 0, 1, 2 or 3, x is an integer ranging from 2 to 6, and $x+z$ cannot be greater than 6.

9. A synthetic lubricating composition according to claim 8 wherein the synthetic lubricant of (A) is at least one cyclopentene of the following formula:

wherein each $R_1$ is individually and independently selected from alkyl groups of 1 to 4 carbon atoms, each $R_2$ is individually and independently selected from hydrocarbyl groups containing 4 to 36 carbon atoms, z is 0, 1, 2 or 3, and x is an integer of 2 to 6, and $x+z$ cannot be greater than 6.

10. A synthetic lubricating composition according to claim 1 wherein the natural lubricant of (B) is a natural lubricant selected from the group consisting of paraffin-type base oils, asphaltic or mixed base crude oils, and mixtures thereof.

11. A synthetic lubricating composition according to claim 1 wherein the synthetic lubricant of (B) is selected from the group consisting of polymerized lower molecular weight alkenes, polymerized esters, phosphates, silicon based lubricants, and mixtures thereof.

12. A synthetic lubricating composition according to claim 1 wherein the lubricating oil additive is contained in the composition in an amount ranging from about 0.01 up to about 40% by weight of the total composition.

13. A synthetic lubricating composition according to claim 12 wherein the additive is selected from the group consisting of pour point depressants, viscosity index improvers, dispersants, load carrying agents, anti-oxidants and mixtures thereof.

14. A synthetic lubricating composition according to claim 12 wherein the additive is selected from the group consisting of zinc dialkyl dithiophosphates, phenates, sulfonates, non-ionic dispersants, polyacrylate pour point dispersants, methacrylate pour point dispersants, olefin copolymer viscosity index improvers, polyacrylate viscosity index improvers, and mixtures thereof.

15. A synthetic lubricating composition according to claim 9 wherein the lubricating oil additive is contained in the composition in an amount ranging from about 0.01 up to about 40% by weight of the total composition.

16. A synthetic lubricating composition according to claim 15 wherein the additive is selected from the group consisting of pour point depressants, viscosity index improvers, and mixtures thereof.

17. A synthetic lubricating composition according to claim 1 wherein the additive is selected from the group consisting of zinc dialkyl dithiophosphates, phenates, sulfonates, non-ionic dispersants, point dispersants, olefin copolymer viscosity index improvers, polyacrylate viscosity index improvers, and mixtures thereof.

* * * * *